United States Patent [19]

Bodenmiller et al.

[11] Patent Number: 5,197,499
[45] Date of Patent: Mar. 30, 1993

[54] PROCESS FOR THE CARE OF MEDICAL AND DENTAL INSTRUMENTS AND MAINTENANCE LOCALE FOR IMPLEMENTING THIS PROCESS

[75] Inventors: Anton Bodenmiller; Pius Steinhauser, both of Leutkirch, Fed. Rep. of Germany

[73] Assignee: Kaltenbach & Voigt GmbH & Co., Biberach/Riss, Fed. Rep. of Germany

[21] Appl. No.: 736,726

[22] Filed: Jul. 26, 1991

[30] Foreign Application Priority Data

Jul. 30, 1990 [DE] Fed. Rep. of Germany ....... 4024171

[51] Int. Cl.⁵ .................................................. B08B 3/10
[52] U.S. Cl. ................................. 134/95.2; 134/102.3; 134/99.2; 134/105; 134/186
[58] Field of Search .................. 134/99, 94, 102, 170, 134/186, 155, 105, 95.2, 100.1, 102.1, 102.2, 102.3; 34/26, 30, 62, 66, 67, 104

[56] References Cited

U.S. PATENT DOCUMENTS

| | | | |
|---|---|---|---|
| 3,070,104 | 12/1962 | Faust et al. | 134/170 X |
| 3,076,468 | 2/1963 | Belt | 134/102 |
| 3,698,024 | 10/1972 | Bruckner | 34/62 X |
| 3,881,503 | 5/1975 | Fox et al. | 134/170 X |
| 3,991,779 | 11/1976 | Saurenman | 134/102 X |
| 4,167,193 | 9/1979 | Magnus et al. | 134/102 X |
| 4,193,818 | 3/1980 | Young et al. | 134/102 X |
| 4,354,514 | 10/1982 | Sundheimer et al. | 134/102 |
| 4,406,297 | 9/1983 | Walton | 134/102 |
| 4,575,951 | 3/1986 | Eyzeguirre | 34/30 |
| 4,708,153 | 11/1987 | Hambleton | 134/178 |

FOREIGN PATENT DOCUMENTS

| | | |
|---|---|---|
| 0173876 | 3/1986 | European Pat. Off. . |
| 1886266 | 10/1963 | Fed. Rep. of Germany . |
| 2035132 | 1/1972 | Fed. Rep. of Germany ...... 134/102 |
| 3601744 | 7/1987 | Fed. Rep. of Germany . |
| 637041 | 7/1983 | Switzerland . |
| 670295 | 7/1979 | U.S.S.R. ............................... 134/102 |

Primary Examiner—Frankie L. Stinson
Attorney, Agent, or Firm—Scully, Scott, Murphy & Presser

[57] ABSTRACT

A process for the care or maintenance of medical and dental instruments and a maintenance locale or installation for implementing this process. The maintenance for the instruments, which is carried out in a single uninterrupted process cycle, and at a single maintenance locale facilitating all of the process steps.

7 Claims, 2 Drawing Sheets

PROCESS FOR THE CARE OF MEDICAL AND DENTAL INSTRUMENTS AND MAINTENANCE LOCALE FOR IMPLEMENTING THIS PROCESS

BACKGROUND OF THE INVENTION

1. Field of the Invention

The present invention relates to a process for the care or maintenance of medical and dental instruments and to a maintenance locale or installation for implementing this process.

2. Discussion or the Prior Art

The disclosure of European Laid-Open Patent Appln. 0173 876 sets forth a method and an arrangement for the cleaning, disinfection and sterilizing of such kinds of instruments; wherein the method is carried out in a container filled with a liquid and with cleaning media while the liquid is subjected to ultrasonic energy during the cleaning procedure. The cleaning is subdivided into a rough or preliminary cleaning and to a fine cleaning, and is then followed by a drying procedure.

The disclosure of German Laid-Open Patent Appln. 36 01 744 teaches a method for the cleaning and disinfection of medical instruments through a program-control automatic rinsing or scavenging installation, whereby a rinsing or scavenging liquid containing heated cleaning and rinsing media is applied by means of a spraying arrangement directed against the instruments which are to be cleaned. Thereafter, there is undertaken a final cleaning and drying procedure.

From the disclosure of Swiss Patent 637,041 there has become known an arrangement for the cleaning of stoppers, in which the process steps provide for cleaning, maintenance with silicon oil, final cleaning, sterilizing and drying. Associated therewith are further process steps in which there are employed detergent solutions.

The brochure "PERO Reinigungs-und Entfettungsautomaten Modell 2500", issued by the German company Hahn & Kolb, discloses a mechanical cleaning and degreasing of non-cuttingly or cuttingly machined metal parts, whereby a re-oiling device is employed for conservation purposes, which conducts solvents enriched with preserving oil over the material being cleaned. The solvent evaporates, the preserving medium remains adherent and forms a protection against corrosion.

From the disclosure of German Petty Patent 18 86 266 there is considered to be known an arrangement for the cleaning of medical instruments, in which stands or uprights are located in the rinsing chamber of a rinsing machine, on which there are supported or from which there are suspended syringes which are to be cleaned.

Inherent to the first-mentioned three processes is the disadvantage that there must be employed detergents or cleaning media, whereby each respective process is lacking in individual important steps.

As a result thereof, the environment is contaminated and the operating personnel subjected to a high workload and; at this time, a plurality of separate apparatuses are required, such that the entire process and the therewith associated installations become complex, cannot be monitored and are resultingly expensive, in which during a possibly required maintenance procedure there is, however, again the effectiveness of the preceding disinfection.

SUMMARY OF THE INVENTION

The invention as described in detail hereinbelow, in the form of a process and also a care or maintenance locale or installation adapted for this purpose, provides the object in the implementation of a complete maintenance or servicing for the instruments, which is carried out in a single uninterrupted process cycle, and at a single maintenance or servicing locale or installation facilitating implementation of all of the process steps.

The advantages which are attainable by means of the present invention lie in that any contamination of the environment is low since chemicals are not required; the operating personnel is under a reduced workload inasmuch as the operation is carried out in a single cycle during the operating sequence; the instruments are again in a state of readiness for their immediate use subsequent to the carrying out of the care or maintenance procedure; and only a single maintenance locale is required so as to result in savings in time and expenditures.

BRIEF DESCRIPTION OF THE DRAWINGS

Reference may now be had to the following detailed description of exemplary embodiments of the inventive process with regard to its individual steps, and the diagrammatic representation of the therewith associated maintenance or care locale; taken in conjunction with the accompanying drawings; in which.

DETAILED DESCRIPTION

Figure 1:
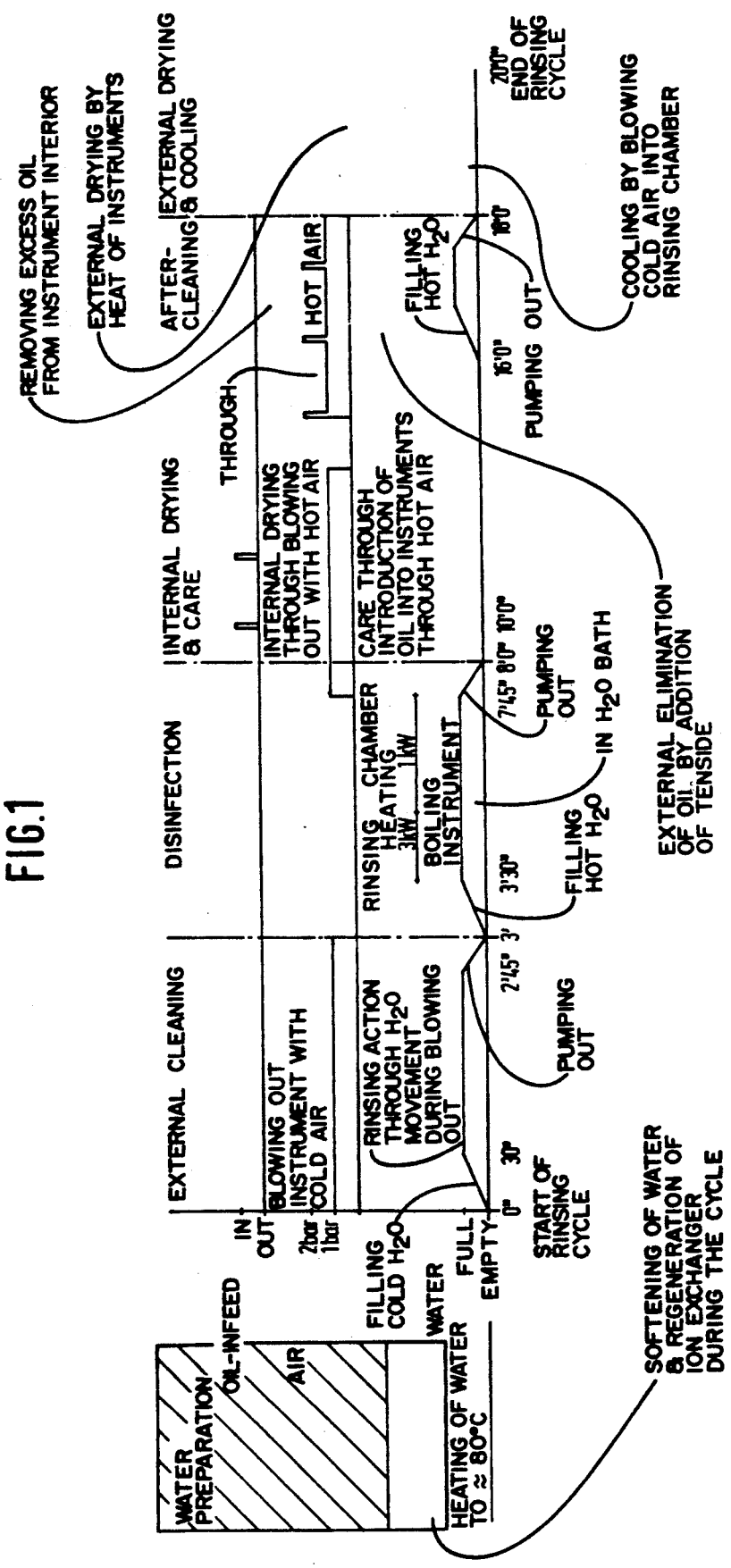
FIG. 1 illustrates a schematic flow diagram of the inventive process.

In FIG. 1 of the drawings, the instruments which are to be cared for or serviced are initially subjected to an external cleaning through the intermediary of being evacuated or blown-through by means of cold air, thereupon there is effected a rinsing action, especially externally through water, which is not displaced by chemicals, and which is placed into circulation through air blasts. The water is first filled in, carries out its rinsing or scavenging action, and is thereafter again pumped-out.

During the next process step, hot water is filled in, which is again without the addition of any chemicals, thereafter the instruments are boiled in the water bath, for which purpose the rinsing chamber is heated, and thereafter the water is pumped-out. In the next segment of the process, the instruments are subjected to an internal drying and to the care or maintenance. Hereby, for this purpose, they are blown-through with hot air and, by means of the hot air, oil is blown into the instruments. The subsequently following final cleaning consists of in the removal of excess oil from the interior of the instruments through the blowing-in of hot air under an increased pressure. The oil remaining on the outside is removed through the intermediary of hot water with tenside additive, which is filled into the rinsing or scavenging chamber, remains a sufficient period of time in the rinsing chamber and is then subsequently pumped-out. The external drying is effected through the inherent or specific heat of the instruments, whose temperature is adequate to eliminate any kind of moistening through vaporization. The subsequently necessary cooling is carried out through a blowing-in of cold air into the rinsing chamber.

The duration of the individual method or process steps is indicated at the individual plotted segments, the entire time for the process consists of about 20 minutes.

The water which is necessary for the process, as shown at the left in the schematic illustration, is softened during the cycle, the ion exchanger regenerated. The water is heated to a temperature of about 80° C. in the boiler.

Figure 2:
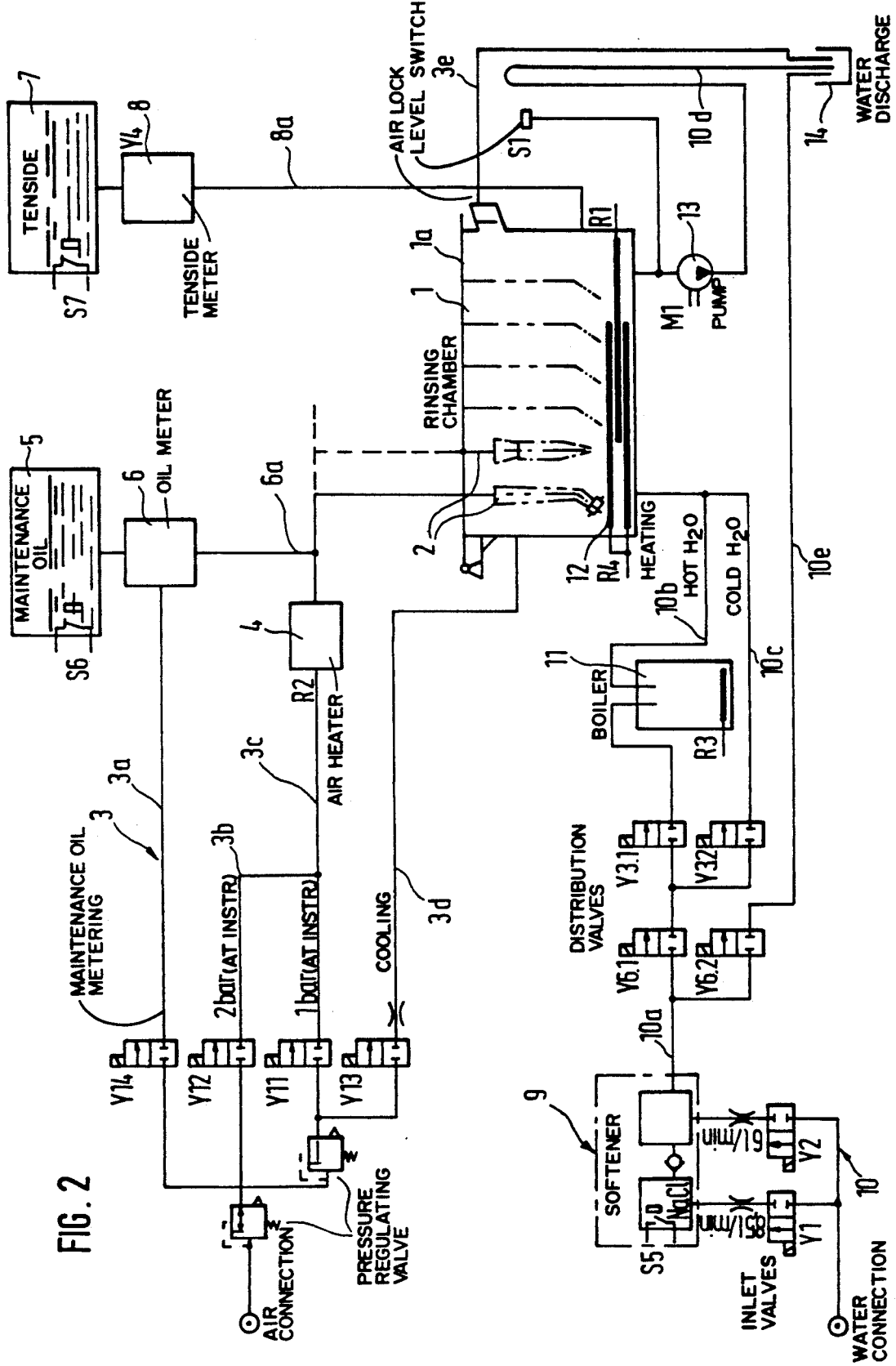
FIG. 2 illustrates a diagrammatic representation of a care or maintenance locale.

In FIG. 2 of the drawings there is elucidated the care or maintenance locale. Herein, the essential element resides in a rinsing or scavenging chamber 1, in which there take place the collective process steps. This locale or installation possesses a removable cover 1a, to which there are attached holders for a specific number of instruments 2, which in this instance are illustrated to represent medical or dental handpieces. Connecting into the holders are air lines for the described process steps, through which air is blown-in. In the rinsing chamber there is provided its own heating system 12.

The air which is to be blown in emanates from an air supply system 3, through which air is conducted from an air inlet connection and a control valve Y 14 without any pretreatment thereof to an oil dosing device 6.

An quantity of air passes through a pressure-regulating valve and a control valve Y 12 into a line 3b, another air quantity through a further control valve Y 11 and a line 3c, both quantities of air are conveyed to an air heater 4. Cooling air is conducted through the lower pressure regulating valve and the control valve Y 13 and the line 3d into the rinsing chamber 1; upon occasion, under a pressure reduction in a throttle. The exhaust air is conducted through the line 3e to a water discharge 14.

A maintenance oil system consists of a container 5 for maintenance or lubricating oil, from which is drawn off to an oil dosing device 6. From there, the dosed oil is conveyed into the line 6a and through this into the line or conduit leading to the holders for the instruments 2.

A tenside system consists of a tenside container 7 and a tenside dosing device 8, from which it is conducted through the line 8a into the rinsing chamber 1.

The water system 10 leads from a water inlet connection through control valves Y 1 and Y 2 for specified flow quantities; when required, through throttles, into a softener 9, in which by means of NaCl and a resin, there is effected a softening action. The path of flow of the water can hereby extend through the NaCl container and the resin container, or alternatively only through the last-mentioned. The water line 10a which exits from the softener 9 leads through the distributor-valves Y 6.1 and Y 3.1 to a boiler 11, and from the latter the hot water is conveyed through the line 10b into the rinsing chamber 1. A branch line, while bypassing the boiler 11, leads cold water through the control valve Y 3.2 directly into the rinsing chamber 1. A further water line conducts excess water through the control valve Y 6.2 directly to the water discharge 14. The manner in which the conductance of air, maintenance oil, tenside and water is carried out during the course of the process can be clearly ascertained from the representation of the process in FIG. 1 of the drawings.

What is claimed is:

1. A maintenance locale for the care and maintenance of medical or dental instruments, comprising a rinsing chamber for the instruments, holders in the rinsing chamber for supporting the instruments, a water supply inlet conduit communicating with the rinsing chamber, a water discharge conduit for discharging water from the rinsing chamber, a heating device for heating the water supplied to said rinsing chamber, supply conduits communicating with the interior of the instruments being associated with said instrument holders, an oil container including oil dosing means which is operatively connected with the supply conduits, a source for pressurized air being connected with the supply conduits, and control means including valves for selectively connecting the oil container and the oil dosing means with the supply conduits.

2. A maintenance locale as claimed in claim 1, wherein said rinsing chamber includes a level control.

3. A maintenance locale as claimed in claim 1, wherein an air supply system has a line for leading cold air to said oil dosing means, conduits for different pressures leading to an air heater; an inlet line for cold air leading to said rinsing chamber; and an exhaust air conduit leading from said rinsing chamber.

4. A maintenance locale as claimed in claim 1, wherein said oil dosing means has cold air conducted thereto for dosing said oil.

5. A maintenance locale as claimed in claim 1, wherein softener means for said water is connected to said water supply inlet conduit, a conduit leading form the softener means to a boiler; an conduit leading from the boiler to the rinsing chamber, a conduit for supplying cold water to the rinsing chamber; a discharge conduit having a pump for conducting waste water for the rinsing chamber to waste water conduits; and an overflow conduit and a water discharge for the waste water conduits.

6. A maintenance locale as claimed in claim 1, comprising a tenside supply system for the introduction of tenside, said system including a tenside container, tenside dosing means connected to said container; and a conduit leading from the tenside dosing means to the rinsing chamber.

7. A maintenance locale as claimed in claim 1, wherein said instruments comprise medical and dental handpieces.

* * * * *